United States Patent [19]

Braid

[11] 4,211,663
[45] Jul. 8, 1980

[54] ALKALI METAL CONTAINING TRANSITION METAL COMPLEXES OF THIOBIS (ALKYLPHENOLS) AS STABILIZERS FOR VARIOUS ORGANIC MEDIA

[75] Inventor: Milton Braid, Westmont, N.J.

[73] Assignee: Mobil Oil Corporation, New York, N.Y.

[21] Appl. No.: 901,875

[22] Filed: May 1, 1978

[51] Int. Cl.$^2$ .................... C10M 1/54; C10M 3/48; C10M 5/28; C10M 7/52
[52] U.S. Cl. ................................. 252/42.7; 44/68; 252/400 R; 260/45.75 C; 260/45.75 M; 260/45.75 N; 260/45.75 P; 260/438.1; 260/439 R
[58] Field of Search ......... 260/438.1, 439 R, 45.75 N, 260/45.75 C, 45.75 P, 45.75 M; 252/42.7, 400 R; 44/68

[56] References Cited

U.S. PATENT DOCUMENTS

| | | | |
|---|---|---|---|
| 2,362,293 | 11/1944 | McNab et al. | 252/42.7 |
| 2,409,687 | 10/1946 | Rogers et al. | 252/42.7 |
| 2,480,664 | 8/1949 | McNab et al. | 252/42.7 |
| 2,518,379 | 8/1950 | Rogers et al. | 252/42.7 |
| 2,673,881 | 3/1954 | Weissberg | 260/438.1 X |
| 2,971,940 | 2/1961 | Fuchsman et al. | 260/45.75 |
| 2,971,941 | 2/1961 | Fuchsman et al. | 260/45.75 |
| 2,971,968 | 2/1961 | Nicholson et al. | 260/439 R |
| 3,210,277 | 10/1965 | Swift | 252/42.7 |
| 3,390,160 | 6/1968 | Heller et al. | 260/438.1 X |
| 4,090,970 | 5/1978 | Braid | 252/42.7 |

*Primary Examiner*—Helen M. S. Sneed
*Attorney, Agent, or Firm*—Charles A. Huggett; Raymond W. Barclay; Howard M. Flournoy

[57] ABSTRACT

Mixed transition metal-alkali metal derivatives of thiobis (alkylphenols) and thiobis (alkylphenol-phenolates) are novel compounds which have utility as oxidation stabilizers for various organic media, e.g., lubricant compositions.

85 Claims, No Drawings

ALKALI METAL CONTAINING TRANSITION METAL COMPLEXES OF THIOBIS (ALKYLPHENOLS) AS STABILIZERS FOR VARIOUS ORGANIC MEDIA

BACKGROUND OF THE INVENTION

1. Field of the Invention

This invention relates to novel compounds comprising mixed alkali metal-transition metal organo-sulfur-containing complexes, e.g., potassium-nickel 2, 2'-thiobis-(4-t-octylphenol-phenolate), having utility as oxidative stabilization additives for various organic media. This invention also relates to synergistic and/or improved mixtures of the afore-mentioned novel compounds and known anti-oxidants such as phenyl-alpha-naphthylamine. Additionally this invention relates to organic compositions, e.g., oils of lubricant viscosity and polyolefin plastic materials, comprising a major proportion of said organic medium and a minor amount of said novel organo-sulfur-containing compounds effective to stabilize said organic medium against oxidative degradation.

DESCRIPTION OF THE PRIOR ART

U.S. Pat. Nos. 2,703,786; 2,716,090 and 3,210,277 disclose the use of polyvalent metal, e.g., Ni salts of alkyl phenol sulfides as oxidation inhibitors and plasticizing agents. Nickel thiobis-(4-t-octylphenolate) is disclosed in U.S. Pat. No. 2,971,940 as a stabilizer for plastics, complexes thereof with amines, e.g., n-butylamine are disclosed in U.S. Pat. No. 3,215,717 as plastics stabilizers. However, there are believed to be no prior art disclosures of thiobis alkylphenolic compounds in accordance herewith.

Foregoing disclosures are directed to organic compositions containing the organosulfur-iron complexes described in accordance with this invention. Further, subject complexes are not disclosed by any prior art known to applicant. Accordingly, their use in various compositions comprising organic media such as oils of lubricant viscosity and plastics to impart resistance to oxidation and other induced degradation is also believed to be novel. They are especially useful in imparting such protection to lubricant base stocks, e.g., paraffinic hydrocarbons, refined petroleum products and synthetic base stock, e.g., ester base stocks.

The oils of lubricating viscosity include greases prepared therefrom and hydrocracked lubricating oils, hydraulic oils, automotive oils, gears oil and transmission fluids and may be mineral oils or fractions thereof and/or synthetic oils of lubricating viscosity or mixtures of mineral and synthetic oils. As mentioned herein above the novel additives of this invention also find utility in plastic materials, e.g., polyolefins such as polypropylene.

SUMMARY OF THE INVENTION

It has been found that transition metal thiobis (alkylphenol-phenolates) are converted by treatment with aqueous alkali metal hydroxide, to mixed alkali-transition metal complexes. For example nickel(II) 2,2'-thiobis-(4-t-octylphenol-phenolate) upon treatment with aqueous potassium hydroxide in converted to novel potassium-containing derivatives with no observable loss or replacement of nickel. It has also been found that di-(transition metal) thiobis (alkylphenolates) may be converted to alkali-containing di-(transition metal) complexes by similar treatment with aqueous alkali metal hydroxide. These derivatives have shown improved antioxidant properties compared with the original transition metal compound, and oxidation inhibiting synergism has been observed in combinations with known antioxidants such as N-phenyl-1-naphthylamine. Furthermore, these alkali metal containing derivatives are soluble in, inter alia, paraffins, refined petroleum lubricating oil base stocks and synthetic ester base stocks and represent a means of solubilizing alkali metals.

This application is also directed to compositions comprising a major proportion of an organic medium normally susceptible to oxidative degradation and a minor amount sufficient to impart antioxidant characteristics and/or ultraviolet stabilization thereto of an alkali metal-transition metal organosulfur-containing complex as described herein below.

The above-described alkali metal-containing transition metal compounds are believed to be novel and the lubricant compositions containing them are also believed to be novel. These derivatives may also be advantageously used in the oxidative stabilization of plastics.

The additive complexes useful in this invention are derived from the following general structures:

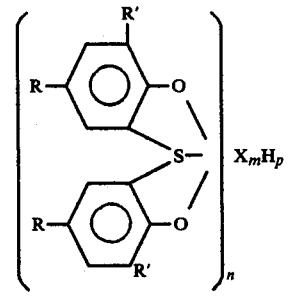

in which R is either hydrogen or an alkyl group having from 1 to about 30 carbon atoms or preferably 1–16 or 4–8 carbon atoms in any isomeric arrangement and R' may be the same as R except that isomers in which the carbon atom attached to the ring is connected to more than two carbon atoms are excluded. X is a transition metal selected from cobalt, iron, nickel and copper, and n=1 to 3, m=1–2, p=0–2.

Representative of the above-described transition metal complexes is Ni[2,2'-thiobis-(4-t-octylphenolate)] having the structure:

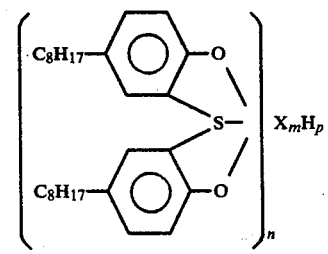

in which $C_8H_{17}$ is 1,1,3,3-tetramethylbutyl.

Additive complexes in accordance herewith are also derived from the following general structures; an equilibrium mixture of two of these isomeric structures may exist.

Structures III, IV, V and VI are representative of those structures having a ratio of transition metal to thiobis(alkylphenol) moiety greater than 1, i.e., 1 to 1.5.

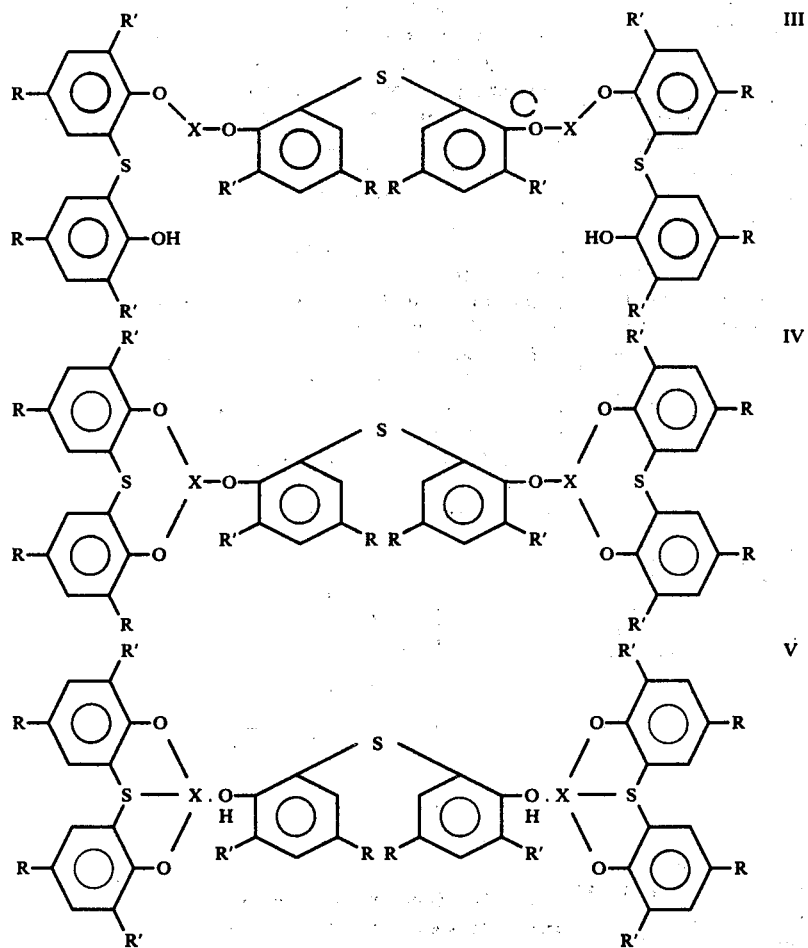

where R, R' and X are as described above. Representative of these complexes is dicobalt tri[2,2'-thiobis-(4-t-octylphenol)] shown below when depicted as structure III.

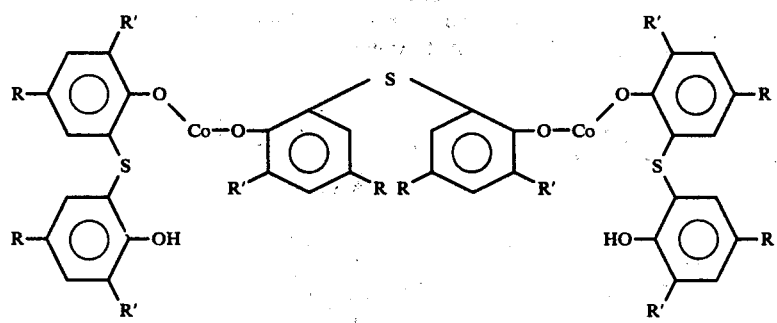

It is also to be understood that there may be obtained complexes which have a higher ratio of alkali metal than transition metal, e.g., dipotassium nickel 2,2'-thiobis-(4-t-octylphenolate).

A preferred embodiment of this invention relates to additive mixtures of the above-described complexes and known amine antioxidants such as phenyl-alpha-naphthylamine (PAN).

Other amines which may be advantageously admixed with the novel complexes embodied herein include alkylated diphenylamines such as alkylated PAN 4,4'-di-t-octyldiphenylamine, phenothiazine, alkoxy- and dialkoxydiphenylamines such as 4-n-octoxy-diphenylamine and 4,4'-dioctoxydiphenylamine.

Preferred are PAN, alkylated PAN, and alkylated diphenylamines. Most preferred are PAN and alkylated diphenylamine.

The transition metal complexes are prepared and/or obtained commercially and thereafter reacted under the general conditions described below to obtain the novel alkali metal-transition metal organosulfur-containing compounds embodied herein.

For example, nickel 2,2'-thiobis-(4-t-octylphenol-phenolate) may be obtained commercially or prepared in accordance with U.S. Pat. No. 2,971,940. The other transition metal complexes, i.e., of iron, copper and cobalt may generally be prepared in appropriate similar manner.

Typically a transition metal organosulfur complex dissolved in a hydrocarbon solvent such as pentane, hexane, cyclohexane, isooctane, etc. is combined with an aqueous solution of alkali metal hydroxide and reacted therewith to produce the novel alkali/transition metal complexes embodied herein.

The novel organosulfur-containing metal/transition metal complexes in accordance with the invention can be effectively employed in any amount which is sufficient for imparting to the organic medium, e.g., lubricant, the desired degree of protection against oxidative degradation. In many instances, the complex is effectively employed in an amount from about 0.01 to about 5%, by weight, of the total weight of the lubricant composition. As herein before indicated, the novel organic sulfur-containing alkali metal/transition metal complexes may be incorporated in any organic media normally subject to oxidative degradation, for example oils of lubricating viscosity or greases prepared thereform in which any of the aforementioned oils or fluids may be employed as vehicles. In general, as previously mentioned synthetic oils can also be effectively protected against oxidative and UV degradation. They may also be protected in combination with mineral oils, or as grease vehicles. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated mineral oils, chaintype polyphenols, siloxanes and silicones (polysiloxanes), alkyl-substituted diphenyl ethers typified by a butyl-substituted bis-(p-phenoxpheny)ether, phenoxy phenylether, etc. Generally speaking it is more particularly concerned with areas of lubricating viscosity, hydrocarbon fuels and fuel oils which may be mineral oils or fractions thereof or synthetic oils as described hereinabove. With respect to synthetic base stock, ester base stock is preferred.

The following examples are not meant to be limiting but to merely exemplify the invention as embodied herein.

EXAMPLE 1

The base oil was synthetic hydrocarbon oil comprising pentaerythritol esters of $C_5$ and $C_9$ or $C_5$ to $C_9$ carboxylic acids. (Table 1)

EXAMPLE 2

Nickel 2,2'-thiobis-(4-t-octylphenol-phenolate) was obtained commercially. Its method of preparation is as described in U.S. Pat. No. 2,971,941.

EXAMPLE 3

Potassium-nickel 2,2'-thiobis-(4-t-octylphenolphenolate) was prepared as follows: using an appropriate aliquot of Example 2.

Nickel 2,2'-thiobis-(4-t-octylphenol-phenolate) (40 g.) prepared in accordance with U.S. Pat. No. 2,971,941 was dissolved in petroleum ether, b.p. 30°–60° C. (500 ml.) and mixed with a solution of potassium hydroxide (22.4 g.) in water (80 ml.). The resulting reaction mixture was stirred for 6.5 hr. at room temperature. The organic layer thereof was washed several times with water, dried and freed of solvent by rotary evaporation. Remaining was a potassium-containing nickel 2,2'-thiobis-(4-t-octylphenol-phenolate), a green solid which softened at 270° C. and melted with decomposition at about 285° C.

Anal. C, 65.17; H, 8.69; S, 6.0; Ni, 7.0; K, 1.4.

EXAMPLE 4

An alternate method of preparing the compound of Example 3 was as follows:

Nickel 2,2'-thiobis-(4-t-octylphenol-phenolate) (10 g.) prepared in accordance with U.S. Pat. No. 2,971,941 and having a melting range of 147°–149° C. was dissolved in petroleum ether, b.p. 30°–60° C. (250 ml.). To this solution was added a solution of potassium hydroxide (5.6 g.) in water (20 ml.) and the resulting reaction mixture was stirred at room temperature for two days and then filtered to remove 0.2 g. of greyish solids. The organic layer was separated from the filtrate's aqueous layer and dried. The petroleum ether solvent was removed by rotary evaporation leaving a potassium-containing nickel 2,2'-thiobis-(4-t-octylphenol-phenolate complex as a green solid melting at about 290° C.

Anal. C, 69.13; H, 8.64; S, 6.08; Ni, 7.4; K, 0.7.

EXAMPLE 5

Lithium-nickel 2,2'-thiobis-(4-t-octylphenol-phenolate) was prepared as described below:

Nickel 2,2'-thiobis-(4-t-octylphenol-phenolate) (40 g.) manufactured commercially under U.S. Pat. No. 2,971,941 was dissolved in petroleum ether b.p. 30°–60° C. (500 ml.) with stirring at room temperature. As stirring of the solution continued, there was added a solution of lithium hydroxide (16.8 g.) in water (80 ml.); the resulting mixture was stirred for an additional 5.5 hr. The organic layer was then separated, washed several times with water, dried and freed of solvent by distillation. The desired product lithium-containing nickel 2,2'-thiobis-(4-t-octylphenol-phenolate) complex was obtained as a green solid residue which softened at 275° C. and decomposed at 300° C.

Anal. C, 66.74; H, 9.06; S, 6.30; Ni, 7.15; Li, 0.9.

EXAMPLE 6

Potassium dicobalt tri-[2,2'-thiobis-(4-t-octylphenol)] was prepared as described below:

Dicobalt tri-[2,2'-thiobis-(4-t-octylphenol)] (14.4 g.) prepared by reaction of cobalt acetate with 2,2'-thiobis-(4-t-octylphenol) as described in our copending U.S. application Ser. No. 847,461 filed Oct. 31, 1977 was dissolved in hexane (100 ml.). While stirring at room temperature a solution of potassium hydroxide (11.2 g.) in water (100 ml.) was added to it. The resulting heterogeneous reaction mixture was stirred for 1.5 hr. The organic layer was separated, combined with hexane extracts of the aqueous layer, dried, and stripped of solvent, to leave the potassium containing dicobalt tri-[2,2'-thiobis-(4-t-octylphenol-phenolate)] complex, a purplish solid mp. 260°–264° C. Changes in the composition of the complex were indicated by the raising of the melting point (reactant, m.p. 115°–118° C.), differences in the infrared spectrum, and changes in elemental analysis including incorporation of potassium.

Anal. Reactant: C, 70.32; H, 8.41; S, 6.66; Co, 8.20; K, O.

Product Complex: C, 64.14; H, 7.77; S, 5.62; Co, 7.0; K, 3.6.

EXAMPLE 7

Sodium-nickel 2,2′-thiobis-(4-t-octylphenol-phenolate) was prepared as follows:

Nickel 2,2′-thiobis-(4-t-octylphenol-phenolate) (40 g.) containing 8% by weight of nickel prepared commercially under U.S. Pat. No. 2,971,941 was dissolved in petroleum ether, b.p. 30°–60° C. (500 ml.). To this solution there was added while stirring at room temperature a solution of sodium hydroxide (16 g.) in water (84 ml.). Initially, a small amount of solids precipitated which redissolved within several minutes. As stirring was continued, the mixture became cloudy again and after a total reaction period of 6.5 hr. the mixture was filtered to remove 0.9 g. of precipitated solids. The organic layer of the filtrate was separated, dried, and solvent-stripped to leave the sodium-containing nickel 2,2′-thiobis-(4-t-octylphenol-phenolate) complex which softened at 275° C. and melted at 300° C.

Anal. Found: C, 65.52; H, 8.35; S, 5.95; Ni, 6.93; Na, 3.4.

EXAMPLE 8

Sodium-dicobalt tri-[2,2′-thiobis-(4-t-octylphenol)] was prepared as follows:

Dicobalt tri-[2,2′-thiobis-(4-t-octylphenol)] complex (14.4 g.) prepared by reaction of cobalt acetate with 2,2′-thiobis-(4-t-octylphenol) as described in our aforementioned co-pending U.S. application Ser. No. 847,461 was dissolved in petroleum ether b.p. 30°–60° C. (100 ml.) To this solution there was added while stirring at room temperature a solution of sodium hydroxide (8 g.) in water (85 ml.). The resulting reaction mixture was stirred at room temperature for a total of 4 hrs. The organic layer was separated, dried, and solvent-stripped to obtain the sodium-containing cobalt 2,2′-thiobis-(4-t-octylphenol) complex, as a purple solid residue, melting point higher than 300° C.

Anal. Reactant: C, 70.32; H, 8.41; S, 6.66; Co, 8.20; Na, O.

Product Complex: C, 68.11; H, 8.26; S, 5.81; Co, 8.05; Na, 1.4.

EXAMPLE 9

Lithium-cobalt tri-[2,2′-thiobis-(4-t-octylphenol)] was prepared as follows:

As described in Example 6 dicobalt tri-[2,2′-thiobis-(4-t-octylphenol)] complex (14.4 g.) was dissolved in petroleum ether b.p. 30°–60° C. To this solution while stirring at room temperature there was added a solution of lithium hydroxide (8.4 g.) in water (80 ml.) and stirring was continued for a total of 5.5 hr. The organic layer was separated, dried, and solvent stripped; lithium-containing cobalt 2,2′-thiobis-(4-t-octylphenol) complex was thus obtained as a brown solid, m.p. 275°–280° C.

Anal. Reactant: C, 70.32; H, 8.41; S, 6.66; Co, 8.20; Li, O.

Product Complex: C, 67.96; H, 8.27; S, 6.08; Co, 8.10; Li, 0.7.

EXAMPLE 10

Preparation of dipotassium-nickel 2,2′-thiobis-(4-t-octylphenolate):

To a solution of potassium hydroxide (12.7 g.) in ethanol (300 ml.) there was added a solution of 2,2′-thiobis-(4-t-octylphenol) (50 g.) in ethanol (200 ml.) To the resulting yellow ethanolic solution there was added a solution of nickel chloride hexahydrate (12.4 g.) in ethanol (175 ml.). The mixture of potassium chloride and dipotassium nickel 2,2′-thiobis-(4-t-octylphenolate) complex which precipitated was collected by filtration. The complex was extracted from the mixture of solids with benzene leaving 8.5 g. of potassium chloride. The benzene solvent was removed by rotary evaporation. The desired potassium-containing complex was obtained as a green solid residue, m.p. higher than 300° C. The elemental analysis corresponded to the composition $K_2Ni(C_{28}H_{40}O_2S)_2$.

Anal. Calc'd. for $C_{56}$, $H_{80}$, $O_4$, $S_2$, $K_2Ni$: C, 66.05; H, 7.92; S, 6.30; Ni, 5.77; K, 7.68. Found: C, 65.63; H, 8.10; S, 6.19; Ni, 5.16; K, 7.11.

An additional amount of the complex was obtained by evaporation of the first ethanolic filtrate and extraction of the dry residue with benzene. Removal of the solvent left a complex with somewhat lower potassium content.

Anal. C, 67.33; H, 8.30; S, 6.05; Ni, 5.53; K, 5.37.

EXAMPLE 11

The base oil (Table 2) was a refined petroleum oil (mineral) base stock.

Various additives in accordance with this invention were evaluated in the Standard Catalytic Oxidation Test (outlined below). They were compared with known antioxidants such as arylamines and with known thiobis(alkylphenols) such as Example 2. They were also evaluated in synergistic and/or improved additive combinations of the novel mixed metal complexes described herein and such known antioxidants.

The known antioxidants include $C_1$–$C_{30}$ alkylamines, arylamines, diarylamines and hindered phenols.

The arylamines used herein are preferably selected from the group consisting of the following: N-phenyl-1-naphthylamine; N-(4′-t-octylphenyl)-1-naphthylamine; N-phenyl-2-naphthylamine; 4,4′-thiobis(N-phenyl-1-naphthylamine); 1,1′-thiobis(N-phenyl-2-naphthylamine); diphenylamine; 4,4′-di-t-octyldiphenylamine; dinaphthylamine; 4-decoxydiphenylamine; phenothiazine. Especially preferred are phenyl naphthylamines such as N-phenyl-1-naphthylamine, N-(4-t-octylphenyl-1-naphthylamine and 4,4′-di-t-octyldiphenylamine.

Any suitable hindered phenol may be used herein. Preferred are those selected from the following non-exhaustive list: 2,6-di-t-butyl-p-cresol; 4,4′-methylenebis(2,6-di-t-butyl-m-cresol); 4,4′-methylenebis(2,6-di-t-butylphenol); 2,6-di-t-butylphenol); 4,4′-butylidenebis(2,6-di-t-butylphenol) and 2,4,6-tri-t-butylphenol. Preferred is 4,4′-methylenebis(2,6-di-t-butylphenol).

The samples were tested in synthetic base stock (Table 1) at 450° F. with a 24-hour air treatment and also in refined petroleum base stock (Table 2) at 325° F. with a 40-hour air treatment. The samples are observed for increase in acidity (NN) and kinematic viscosity (KV) after treatment, the loss in weight of the lead specimen and the relative amount of visual sludge. The test procedure is described herein below.

CATALYTIC OXIDATION TEST

A sample of the base lubricant is placed in an oven at a desired temperature. Present in the sample are the following metals either known to catalyze organic oxidation or commonly used materials of construction.
 a. 15.6 sq. in. of sand-blasted iron wire,
 b. 0.78 sq. in. of polished copper wire,
 c. 0.87 sq. in. of polished aluminum wire, and
 d. 0.167 sq. in. of polished lead surface.

Dry air is passed through the sample at a rate of about 5 liters per hour.

The data from this test are recorded below in the Tables. These data which include prior art compounds illustrate the unexpected and surprising superiority of compounds in accordance with this invention over such prior art compounds.

While this invention has been described with reference to preferred compositions and components therefor, it will be understood by those skilled in the art that departure from the preferred embodiments can be effectively made and are within the scope of the specification.

TABLE 1
CATALYTIC OXIDATION TEST
450° F. 24 HR., PENTAERYTHRITOL ESTERS OF $C_5$ AND $C_9$ CARBOXYLIC ACIDS

| Additive | Conc., Wt.% | ΔNN | ΔKV % | Lead Metal Loss, mg. | Sludge |
|---|---|---|---|---|---|
| Example 1: None | — | 8.25 | 586 | 13.7 | Trace |
| Example 2: Nickel 2,2'-thiobis-(4-t-octylphenol-phenolate) | 2 | 4.2 | 92 | 1.3 | Nil |
|  | 1 | 4.98 | 119 | 1.4 | Nil |
| Example 3: Potassium-nickel 2,2'-thiobis-(4-t-octylpheol-phenolate) | 1 | 6.3 | 23 | 4 | Mod. |
| Example 4: Potassium-nickel, 2,2'-thiobis-(4-t-octylphenol-phenolate) | 2 | 1.83 | 48 | 5.7 | Light |
| Example 4 | 1 | 2.13 | 52 | 4.6 | Nil |
| Example 4 + N-phenyl-1-naphthylamine | 1 / 1 | 1.75 | 34 | 3.4 | Nil |
| Example 4 + N-phenyl-1-naphthylamine | 1 / 0.5 | 1.7 | 35 | 3.5 | Nil |
| PAN (N-phenyl-1-naphthylamine) | 2 | 3.6 | 82 | 0.2 | Light |
| Example 5: Lithium-nickel 2,2'-thiobis-(4-t-octylphenol-phenolate) | 2 | 1.8 | 54 | 2.9 | Mod. |
|  | 1 | 3.6 | 97 | 2.1 | Nil |
| Example 5 + N-phenyl-1-naphthylamine | 1 / 1 | 1.95 | 40 | 2.8 | Nil |
| Example 6: Potassium-dicobalt tri-2,2'-thiobis-(4-t-octylphenol) complex | 2 | 1.7 | 37 | 2.8 | Light |
|  | 1 | 2.3 | 33 | 3.7 | Nil |
| Example 6 + N-phenyl-1-naphthylamine | 1 / 1 | 1 | 26 | 3.4 | Mod. |

TABLE 2
CATALYTIC OXIDATION TEST
325° F. 40 HR., REFINED PETROLEUM BASE STOCK

| Additive | Conc., Wt.% | ΔNN | ΔKV % | Lead Metal Loss, mg. | Sludge |
|---|---|---|---|---|---|
| None | — | 17 | 334 | 66 | Heavy |
| Example 3 | 1 | 5.6 | 88 | 0.4 | Heavy |
|  | 0.5 | 6.1 | 75 | 1 | Heavy |
|  | 0.25 | 5.1 | 62 | 6 | Heavy |
| Example 3 + 4,4'-Methylenebis-(2,6-di-t-butylphenol) | 0.25 / 0.5 | 4.6 | 36 | — | Heavy |
| Example 5 | 1 | 5.2 | 84 | 2.5 | Heavy |
|  | 0.5 | 5.4 | 71 | — | Heavy |
|  | 0.25 | 6.7 | 66 | 1.1 | Heavy |
| Example 5 + N-phenyl-1-naphthylamine | 0.5 / 1 | 4.3 | 28 | 0.5 | Heavy |
| Example 6 | 1 | 8.4 | 56 | — | Moderate |
|  | 0.5 | 9.4 | 94 | — | Heavy |
|  | 0.25 | 9.9 | 87 | — | Heavy |
| Example 6 + 4,4'-di-t-octyldiphenylamine | 1 / 0.5 | 1.47 | 11 | 3.6 | Light |
| 4,4'-Methylenebis-(2,6-di-t-butylphenol) | 1 | 5.2 | 47 | — | Heavy |
| N-phenyl-1-naphthylamine | 2 | 0.26 | 31 | 0.2 | Light |
| 4,4'-di-t-octyldiphenylamine | 2 | 1.3 | 18 | 0.3 | Light |

I claim:

1. A mixed alkali metal-transition metal organosulfur-containing complex derived from transition metal complexes having the following general structures:

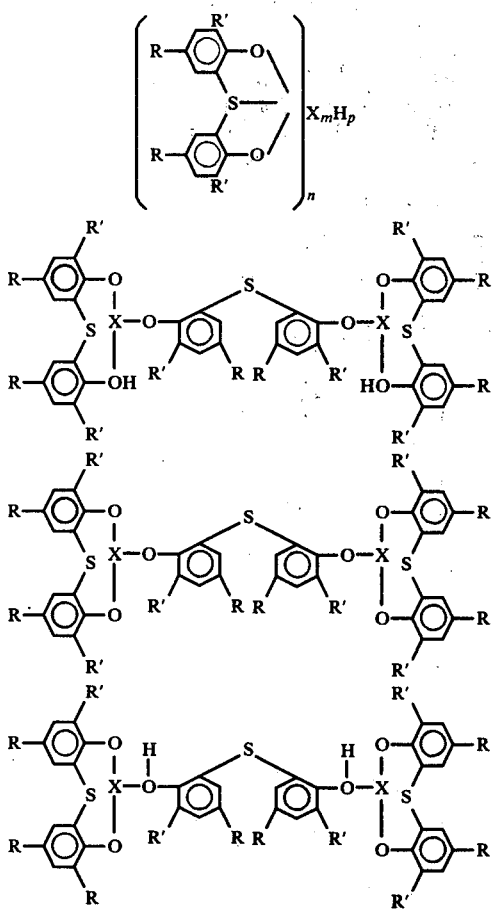

in which R is either hydrogen or an alkyl group having from 1 to about 30 carbon atoms in any isomeric arrangement and R' may be the same as R except that isomers in which the carbon atom attached to the ring is connected to more than two carbon atoms are excluded, and wherein the alkali metal is selected from sodium, potassium and lithium, X is a transition metal selected from nickel, iron, copper and cobalt and n is 1 to 3, m is 1 to 2 and p is 0 to 2.

2. The mixed metal complex of claim 1 derived from a transition metal complex in which each R is an alkyl group containing from 4 to 16 carbon atoms and each R' is hydrogen.

3. The complex of claim 2 in which each R thereof is an alkyl group and contains 8 carbon atoms.

4. The complex of claim 3 in which each alkyl group thereof is a 4-t-octyl radical.

5. The complex of claim 4 in which each alkyl group is 1,1,3,3-tetramethylbutyl.

6. The mixed metal complex of claim 1 derived from structure I wherein the transition metal thereof is selected from nickel and cobalt, m is 1, n is 2, p is 0 and R' is hydrogen.

7. The complex of claim 6 wherein the alkali metal is potassium and the transition metal is nickel.

8. The complex of claim 7 in which each R thereof is an alkyl group having from 4–16 carbon atoms.

9. The complex of claim 8 in which each alkyl group thereof is a 4-t-octyl radical.

10. The complex of claim 9 in which each alkyl group is 1,1,3,3-tetramethylbutyl.

11. The complex of claim 7 having a 2 to 1 ratio of potassium to nickel.

12. The complex of claim 6 wherein the alkali metal is potassium and the transition metal is cobalt.

13. The complex of claim 12 in which each R thereof is an alkyl group having from 4–16 carbon atoms.

14. The complex of claim 13 in which each alkyl group thereof is a 4-t-octyl radical.

15. The complex of claim 14 in which each alkyl group is 1,1,3,3-tetramethylbutyl.

16. The complex of claim 6 wherein the alkali metal is lithium and the transition metal is nickel.

17. The complex of claim 16 in which each R thereof is an alkyl group having from 4–16 carbon atoms.

18. The complex of claim 17 in which each alkyl group thereof is a 4-t-octyl radical.

19. The complex of claim 18 in which each alkyl group is 1,1,3,3-tetramethylbutyl.

20. The complex of claim 6 wherein the alkali metal is lithium and the transition metal is cobalt.

21. The complex of claim 20 in which each R thereof is an alkyl group having from 4–16 carbon atoms.

22. The complex of claim 21 in which each alkyl group thereof is a 4-t-octyl radical.

23. The complex of claim 22 in which each alkyl group is 1,1,3,3-tetramethylbutyl.

24. The complex of claim 6 wherein the alkali metal is sodium and the transition metal is nickel.

25. The complex of claim 24 in which each R thereof is an alkyl group having from 4–16 carbon atoms.

26. The complex of claim 25 in which each alkyl group thereof is a 4-t-octyl radical.

27. The complex of claim 26 in which each alkyl group is 1,1,3,3-tetramethylbutyl.

28. The complex of claim 6 wherein the alkali metal is sodium and the transition metal is cobalt.

29. The complex of claim 28 in which each R thereof is an alkyl group having from 4–16 carbon atoms.

30. The complex of claim 29 in which each alkyl group thereof is a 4-t-octyl radical.

31. The complex of claim 30 in which each alkyl group is 1,1,3,3-tetramethylbutyl.

32. The mixed metal complex of claim 1 wherein said complex is derived from the group consisting of structures II, III and IV wherein the transition metal thereof is selected from nickel and cobalt and R' is hydrogen.

33. The complex of claim 32 wherein the alkali metal is potassium and the transition metal is nickel.

34. The complex of claim 33 in which each R thereof is an alkyl group having from 4–16 carbon atoms.

35. The complex of claim 34 in which each alkyl group thereof is a 4-t-octyl radical.

36. The complex of claim 35 in which said alkyl group is 1,1,3,3-tetramethylbutyl.

37. The complex of claim 32 wherein the alkali metal is potassium and the transition metal is cobalt.

38. The complex of claim 37 in which each R thereof is an alkyl group having from 4–16 carbon atoms.

39. The complex of claim 38 in which each alkyl group thereof is a 4-t-octyl radical.

40. The complex of claim 39 in which said alkyl group is 1,1,3,3-tetramethylbutyl.

41. The complex of claim 32 wherein the alkali metal is lithium and the transition metal is nickel.

42. The complex of claim 41 in which each R thereof is an alkyl group having from 4–16 carbon atoms.

43. The complex of claim 42 in which each alkyl group thereof is a 4-t-octyl radical.

44. The complex of claim 43 in which said alkyl group is 1,1,3,3-tetramethylbutyl.

45. The complex of claim 32 wherein the alkali metal is lithium and the transition metal is cobalt.

46. The complex of claim 45 in which each R thereof is an alkyl group having from 4–16 carbon atoms.

47. The complex of claim 46 in which each alkyl group thereof is a 4-t-octyl radical.

48. The complex of claim 47 in which said alkyl group is 1,1,3,3-tetramethylbutyl.

49. The complex of claim 32 wherein the alkali metal is sodium and the transition metal is nickel.

50. The complex of claim 49 in which each R thereof is an alkyl group having from 4–16 carbon atoms.

51. The complex of claim 50 in which each alkyl group thereof is a 4-t-octyl radical.

52. The complex of claim 51 in which said alkyl group is 1,1,3,3-tetramethylbutyl.

53. The complex of claim 32 wherein the alkali metal is sodium and the transition metal is cobalt.

54. The complex of claim 53 in which each R thereof is an alkyl group having from 4–16 carbon atoms.

55. The complex of claim 54 in which each alkyl group thereof is a 4-t-octyl radical.

56. The complex of claim 55 in which said alkyl group is 1,1,3,3-tetramethylbutyl.

57. A composition comprising a major proportion of an organic medium normally susceptible to oxidative degradation and a minor amount sufficient to impart antioxidant properties and/or ultraviolet stabilization thereto of an organosulfur-containing alkali metal-transition metal complex as described in claim 1.

58. The composition of claim 15 in which the alkyl groups contain from 4 to about 16 carbon atoms.

59. The composition of claim 58 in which each alkyl group contains 8 carbon atoms.

60. The composition of claim 59 in which each alkyl group is a 4-t-octyl radical.

61. The composition of claim 60 in which each alkyl group is 1,1,3,3-tetramethylbutyl.

62. The composition of claim 57 wherein the organic medium is selected from plastics and oils of lubricating viscosity or greases prepared therefrom, said oils include hydrocracked oils, hydraulic oils, automotive oils, gear oils, transmission fluids, waxes and plastics and wherein said oils may be mineral oils and fractions thereof or synthetic hydrocarbon base oils.

63. The composition of claim 62 wherein the organic medium is an oil of lubricating viscosity.

64. The composition of claim 63 wherein the oil is further characterized as a mineral oil.

65. The composition of claim 63 wherein the oil is further characterized as a synthetic hydrocarbon base oil.

66. The composition of claim 65 wherein the synthetic hydrocarbon base oil is derived from pentaerythritol esters of $C_5$ and $C_9$ or $C_5$–$C_9$ carboxylic acids.

67. The composition of claim 57 in which the organosulfur-containing alkali metal-transition metal complex is derived from structure I wherein the transition metal thereof is selected from nickel and cobalt, m is 1, n is 2, p is 0, and R' is hydrogen.

68. The composition of claim 67 in which each R thereof is an alkyl group having from 4–16 carbon atoms.

69. The composition of claim 68 in which each alkyl group thereof is a 4-t-octyl radical.

70. The composition of claim 69 in which said alkyl group is 1,1,3,3-tetramethylbutyl.

71. The composition of claim 57 in which the organosulfur-containing alkali metal-transition metal complex is derived from the group consisting of structures II, III and IV wherein the transition metal is selected from nickel and cobalt and R' is hydrogen.

72. The composition of claim 71 wherein each R thereof is an alkyl group having from 4 to 16 carbon atoms.

73. The composition of claim 72 in which each alkyl group thereof is a 4-t-octyl radical.

74. The composition of claim 73 in which said alkyl group is 1,1,3,3-tetramethylbutyl.

75. A composition comprising a major proportion of an organic medium normally susceptible to oxidative degradation and a minor amount sufficient to impart antioxidant properties and/or ultraviolet stabilization thereto of an admixture of an organosulfur-containing alkali metal-transition metal complex as described in claim 1 and a $C_1$–$C_{30}$ alkylamine or an aryl amine.

76. The composition of claim 75 in which the amine is an aryl amine.

77. The composition of claim 76 in which the amine is N-phenyl-1-naphthylamine.

78. The composition of claim 77 in which the organosulfur-containing alkali metal-transition metal complex is potassium-nickel 2,2'-thiobis-(4-t-octyl-phenol-phenolate).

79. The composition of claim 77 in which the organosulfur-containing metal complex is lithium-nickel 2,2'-thiobis(4-t-octylphenol-phenolate).

80. The composition of claim 79 in which the organosulfur-containing metal complex is potassium-dicobalt tri-[2,2'-thiobis-(4-t-octylphenol)].

81. An additive combination comprising an organosulfur containing complex as described in claim 1 and a mixture thereof consisting of said complex and an aryl or $C_1$–$C_{30}$ alkyl amine.

82. The additive combination of claim 81 wherein said amine is an aryl amine.

83. The additive combination of claim 82 wherein said amine is N-phenyl-1-naphthylamine.

84. The additive combination comprising an organosulfur-containing complex as described in claim 1 and a mixture thereof consisting of said complex and a hindred phenol.

85. The additive combination of claim 84 wherein said hindered phenol is 4,4'-methylenebis(2,6-di-t-butylphenol).

* * * * *